United States Patent [19]

Kramer et al.

[11] Patent Number: 4,847,089
[45] Date of Patent: Jul. 11, 1989

[54] CLEANSING AND DISINFECTING COMPOSITIONS, INCLUDING BLEACHING AGENTS, AND SPONGES AND OTHER APPLICATORS INCORPORATING THE SAME

[75] Inventors: David N. Kramer, 2119 Wiltonwood Rd., Stevenson, Md. 21153; Philip A. Snow, Henderson, Md.

[73] Assignee: David N. Kramer, Stevenson, Md.

[21] Appl. No.: 86,876

[22] Filed: Aug. 19, 1987

Related U.S. Application Data

[63] Continuation-in-part of Ser. No. 886,171, Jul. 16, 1986.

[51] Int. Cl.[4] .......................................... A01H 25/00
[52] U.S. Cl. ................................. 424/405; 424/411; 15/104.93
[58] Field of Search .................. 424/5, 11, 446, 447; 15/104.93

[56] References Cited

U.S. PATENT DOCUMENTS

| | | | |
|---|---|---|---|
| 916,692 | 3/1909 | Von Foregger . | |
| 959,605 | 5/1910 | Quissey | 424/53 |
| 975,129 | 11/1910 | Gruter et al. | 252/186.31 |
| 975,353 | 11/1910 | Gruter et al. | 252/186.31 |
| 1,576,774 | 3/1926 | McGraw | 424/62 |
| 2,015,179 | 9/1935 | McGraw | 167/91 |
| 2,086,585 | 7/1937 | Taub et al. | 260/127 |
| 2,087,131 | 8/1937 | Taub et al. | 260/127 |
| 2,228,483 | 1/1941 | Raeke | 23/6 |
| 2,377,066 | 5/1945 | Baird et al. | 252/98 |
| 2,432,114 | 12/1947 | Marquand | 167/72 |
| 2,527,686 | 10/1950 | Sandberg | 167/93 |
| 2,542,909 | 2/1951 | De Wet | 167/84 |
| 2,882,237 | 4/1959 | Mahoney | 252/186 |
| 2,917,428 | 12/1959 | Hitzman | 42/41 |
| 2,926,119 | 2/1960 | Niederhanser | 167/30 |
| 2,933,453 | 4/1960 | Burks | 252/412 |
| 2,989,484 | 6/1961 | Kirstahler et al. | 252/110 |
| 3,265,624 | 8/1966 | Inamorato | 252/99 |
| 3,283,357 | 11/1966 | Decker et al. | 424/411 |
| 3,337,466 | 8/1967 | Puetzer et al. | 252/99 |
| 3,378,444 | 4/1968 | Swanson | 167/88 |
| 3,441,507 | 4/1969 | Schiefer et al. | 252/95 |
| 3,562,165 | 2/1971 | Altieri | 252/99 |
| 3,565,294 | 2/1971 | Schwartzman | 222/107 |
| 3,651,931 | 3/1972 | Hsaing | 206/47 A |
| 3,684,722 | 8/1972 | Hynam et al. | 252/98 |

(List continued on next page.)

FOREIGN PATENT DOCUMENTS

| | | |
|---|---|---|
| 1067411 | 11/1975 | Canada . |
| 3248 | 11/1977 | European Pat. Off. . |
| 55386 | 12/1980 | European Pat. Off. . |
| 20660682 | 6/1981 | Japan . |
| 22200883 | 6/1982 | Japan . |
| 7907552 | 10/1978 | Netherlands . |

Primary Examiner—Thurman K. Page
Assistant Examiner—L. R. Horne
Attorney, Agent, or Firm—Leonard Bloom

[57] ABSTRACT

A cleansing and disinfecting composition comprising an alkaline per-salt and a positively charged phase-transfer agent and absorbent materials, such as sponges, impregnated therewith. The composition preferably also contains one or more surfactants. The alkaline per-salt is an alkaline water-soluble salt having hydrogen peroxide of crystallization. The positively charged phase-transfer agent is preferably a quaternary ammonium salt. The composition may be formulated as a cream, a bulk powder, a solution or tablets. It may also be incorporated in wipes, sponges and brushes. In one embodiment, one surface of the impregnated sponge is an abrasive material. The compositions of this invention find utility in health care, as disinfectants in surgical applications, and as cleansing and decontaminating agents. Specific uses include skin cleansing and disinfecting, treatment for exposure to toxic plants such as poison ivy, treatment for exposure to industrial and agricultural chemicals such as herbicides and pesticides, and cleansing and disinfecting surfaces and sensitive equipment. The impregnated sponges may be stored indefinitely and activated by the addition of water. They are adapted to being dispensed for on-the-spot use as stain or spot removers and may include bleaching or whitening agents.

26 Claims, 2 Drawing Sheets

U.S. PATENT DOCUMENTS

| | | | |
|---|---|---|---|
| 3,716,499 | 2/1973 | Inamorato | 252/524 |
| 3,730,912 | 5/1973 | Inamorato | 252/528 |
| 3,756,775 | 9/1973 | Nordfalt | 8/111 |
| 3,811,833 | 5/1974 | Stalter | 8/111 |
| 3,829,329 | 8/1974 | O'Driscoll et al. | 134/26 |
| 3,922,099 | 11/1975 | Christine et al. | 401/134 |
| 3,953,350 | 4/1976 | Fujino et al. | 252/94 |
| 3,954,974 | 5/1976 | Herzog et al. | 424/130 |
| 4,049,354 | 9/1977 | O'Rourke | 401/134 |
| 4,056,611 | 11/1977 | Young | 424/62 |
| 4,124,518 | 11/1978 | Stone et al. | 15/104.93 |
| 4,150,113 | 4/1979 | Hoogendoorn et al. | 424/50 |
| 4,247,537 | 1/1981 | Lunn et al. | 424/62 |
| 4,259,383 | 3/1981 | Eggensperger et al. | 428/72 |
| 4,289,728 | 9/1981 | Peel et al. | 422/24 |
| 4,296,103 | 10/1981 | Laso | 424/130 |
| 4,313,932 | 2/1982 | Watts | 424/62 |
| 4,329,245 | 5/1982 | Eymond et al. | 252/102 |
| 4,337,163 | 6/1982 | Schlip | 252/96 |
| 4,362,639 | 12/1982 | Eoga | 252/99 |
| 4,397,757 | 8/1983 | Bright et al. | 252/186.41 |
| 4,451,384 | 5/1984 | Malafosse | 252/102 |
| 4,470,919 | 9/1984 | Goffinet et al. | 252/102 |
| 4,476,108 | 10/1984 | Kessler | 424/50 |
| 4,507,278 | 3/1985 | DeMarco et al. | 424/62 |
| 4,525,292 | 6/1985 | Cashman et al. | 252/102 |

CLEANSING AND DISINFECTING COMPOSITIONS, INCLUDING BLEACHING AGENTS, AND SPONGES AND OTHER APPLICATORS INCORPORATING THE SAME

CROSS REFERENCE TO RELATED APPLICATION

The present application is a continuation-in-part of U.S. patent application Ser. No. 886,171 filed on July 16, 1986, the contents of which are incorporated by reference herein in its entirety.

FIELD OF THE INVENTION

This invention relates to cleansing and disinfecting compositions which find utility in health care, as disinfectants in surgical applications and as decontaminating agents, and particularly, to cleansing sponges incorporating such cleansing and disinfecting compositions. The cleansing sponges of this invention find particular utility as spot and stain removers and exhibit a number of advantages over presently-available liquid detergents and stain removers.

BACKGROUND OF THE INVENTION

There is a constant need for cleansing and disinfecting compositions for use in the health care field, as disinfectants in surgical applications and as decontaminating agents. For example, in the health care field there is a need for cleansers and skin exfoliants, antiviral agents, fungicides and bactericides for the treatment and control of such disorders as acne, athlete's foot and dandruff. There is also a need for topical products to give relief to those suffering from insect stings, poison ivy and poison oak. In the surgical field, a need exists for soaps and impregnated sponges for cleansing and disinfecting the skin of surgeons and patients. A need also exists for disinfectant solutions for cleansing and disinfecting the skin as well as for the disinfecting of surgical instruments. Among household and industrial needs are cleansers, algicides for swimming pools, decontaminating agents for pesticide and chemical spills, and stain and spot removers that may be used on a wide variety of substrates. A particular need exists for sponges impregnated with a cleansing and disinfecting composition, and which can be readily activated merely by the addition of water.

There are many cleansing and disinfecting agents currently in use. However, most of these agents suffer from one or more deficiencies. The deficiencies, one or more of which are exhibited by many currently used cleansing and disinfecting agents, include skin irritation; offensive or irritating odor and inhalation toxicity; corrosiveness toward metal; fabrics and painted surfaces; lack of stability; and low level of efficacy.

The prior art also includes U.S. Pat. No. 2,917,428, which discloses an aqueous disinfecting composition containing a quaternary ammonium halide, hydrogen peroxide and acetate salts of saturted acyclic amines, which are slightly acidic. Since the aqueous medium must be alkaline, e.g., having a pH equal to or greater than ca. 9.5 before a proton can be extracted from hydrogen peroxide to a significant extent, i.e., approximately half ionized, the compositions in U.S. Pat. No. 2,917,428 cannot form the quaternary ammonium hydroperoxide phase-transfer complex which is critical to the instant invention.

SUMMARY OF THE INVENTION

The cleansing and disinfecting compositions of this invention exhibit a number of improvements over prior art compositions. The components of the cleansing and disinfecting compositions of this invention are readily available and relatively inexpensive. The compositions of this invention are not irritating to the skin or absorbed through the skin or mucous membranes. They do not have an offensive or irritating odor and are, in fact, non-volatile. Moreover, the compositions are not corrosive toward metals, fabrics or painted surfaces and are, in many instances, anti-corrosive. In addition, the compositions exhibit a high level of efficacy as rapid cleansing and disinfecting agents and have excellent stability characteristics.

Absorbent materials such as sponges having incorporated therein the cleansing and disinfecting compositions of this invention find utility in cleansing and disinfecting the skin of, for example, surgeons and patients, as well as in cleansing and disinfecting various surfaces in need thereof. The impregnated sponges are effective against a large number of stains, may be stored almost indefinitely and may be activated by the addition of water. They are thus portable and accordingly lend themselves to being dispensed in hotel rooms, restaurants, laundry establishments, travel kits, clothing stores, fabric and sewing stores, and by airlines. The impregnated sponges of this invention may, if desired, have an abrasive surface.

It is therefore an object of this invention to provide improved cleansing and disinfecting compositions.

It is another object of this invention to provide cleansing and disinfecting compositions made from readily available and relatively inexpensive components.

It is still another object of this invention to provide cleansing and disinfecting compositions that are not irritating to the skin.

It is yet another object of this invention to provide cleansing and disinfecting compositions that do not have an offensive or irritating odor.

Another object of this invention is to provide cleansing and disinfecting compositions that are not corrosive toward metals, fabrics or painted surfaces.

Still another object of this invention is to provide highly efficacious and rapid cleansing and disinfecting compositions.

Yet another object of this invention is to provide cleansing and disinfecting compositions having excellent stability characteristics.

It is still another object of this invention to provide sponges impregnated with (or otherwise suitably incorporating) the cleansing and disinfecting compositions of this invention.

It is yet still another object of this invention to provide sponges containing a bleaching and/or whitening agent.

Another object of this invention is to provide sponges impregnated with the cleansing and disinfecting compositions of this invention and wherein said sponges have an abrasive surface.

The foregoing and other objects are accomplished by the practice of this invention. Broadly, viewed in one of its principal aspects, this invention consists of an absorbent material impregnated with a cleansing and disinfecting composition, said composition comprising an alkaline water-soluble salt having hydrogen peroxide of crystallization and a positively charged phase-transfer agent.

The foregoing cleansing and disinfecting composition and absorbent materials impregnated therewith may be used in a method to cleanse or disinfect a substrate in need thereof comprising contacting said substrate with an aqueous solution of an alkaline water-soluble salt having hydrogen peroxide of crystallization and a positively charged phase-transfer agent or with a wet absorbent material impregnated with an alkaline water-soluble salt having hydrogen peroxide of crystallization and a positively charged phase-transfer agent.

The instant invention thus provides cleansing and disinfecting compositions as well as sponges impregnated with said cleansing and disinfecting compositions that find utility in health care, as disinfectants in surgical applications and as effective cleansing and decontaminating agents useful on a broad spectrum of substrates. The compositions of this invention are characterized by not being irritating to the skin, by not having an offensive or irritating odor, by not being corrosive, by having excellent stability, and by being rapid and highly effective cleansing and disinfecting agents. Sponges having incorporated therein the compositions of this invention are characterized by the timed release of the active ingredients and by the ability to provide effective activity with repeated use. The impregnated sponges of this invention have a long shelf life, may be activated by the addition of water, and are effective against a wide variety of stains.

The nature and substance of the present invention as well as its objects and advantages will be more clearly perceived and fully understood by referring to the following description and claims taken in connection with the accompanying drawings which are described briefly below.

DESCRIPTION OF THE PREFERRED EMBODIMENTS

Figure 1:
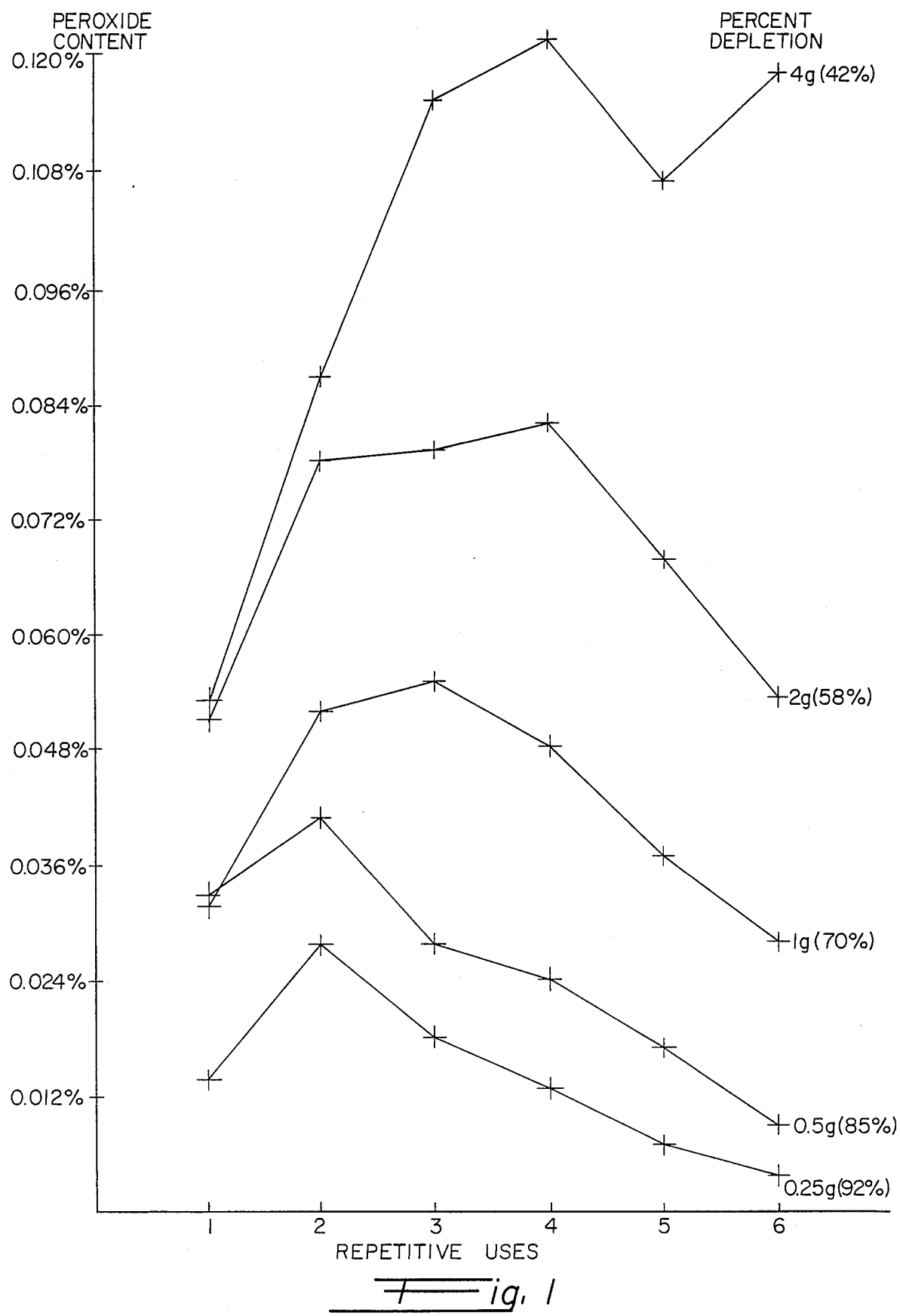
FIG. 1 is a graph showing the timed release of peroxide from a sponge containing a cleansing composition of the invention which is subjected to a series of water washings.

The cleansing and disinfecting compositions of this invention are thus characterized by having broad utility, for example, in health care, as disinfectants in surgical applications and as cleansing and decontaminating agents. The compositions of this invention comprise an alkaline water-soluble salt having hydrogen peroxide of crystallization and a positively charged phase-transfer agent. Depending on the intended use, the compositions of this invention may also contain various additives. For example, the compositions may advantageously contain a surfactant. The compositions may also contain peroxide activators such as enzymes, iodides, and hemin; perfumes such as rose oil; dyes such as fluorescein; emolients such as lanolin and glycol derivatives; gelling agents such as carboxymethyl cellulose; clays such as kaolinite, attapulgite and bentonite; and metal peroxides such as calcium peroxide. Examples of suitable enzymes are horseradish peroxidase, lactoperoxidase and myeloperoxidase. Activators also include organic per acid formation; e.g., penta acetyl glucose and tetra acetyl ethylenediamine.

The compositions of this invention may be compounded in various forms suitable for particular end uses. Thus, the compositions may be formulated as creams, bulk powders, tablets, soaps, and solutions. In addition, they may be incorporated into wipes, sponges and brushes. In one embodiment of the invention, the sponge containing the cleansing and disinfecting composition may have an abrasive surface.

The per-salts used in the practice of this invention are alkaline water-soluble salts having hydrogen peroxide of crystalization or forms peroxide upon dissociation. When the salts are dissolved in water, peroxide ion is released. Examples of suitable per-salts are percarbonates, perborates, persilicates and perphosphates associated with a cation that will give an alkaline water-soluble salt. Examples of suitable cations are the alkali metals. Especially preferred is sodium percarbonate having the empirical formula $2Na_2CO_3.3H_2O_2$, sodium percarbonate having the hydrogen peroxide of crystallization.

It should be noted that per-salts alone are excellent disinfectants and are superior to hydrogen peroxide in this regard. Hydrogen peroxide is a weak disinfectant and has poor permeability into bacteria. On the other hand, when a per-salt is dissolved in water and liberates hydrogen peroxide, the alkaline salt extracts a proton from the liberated hydrogen peroxide forming the hydroperoxide ion. The hydroperoxide ion, in contrast to hydrogen peroxide, is a strong disinfectant and is readily permeable into bacteria.

The positively charged phase-transfer agent may be a phosphonium salt such as t-butyl phosphonium iodide, a sulfonium salt such as tributyl sulfonium chloride, or a quaternary ammonium salt. The choice of the positively charged phase-transfer agent is critical. The choice of the counter anion of the positively charged phase-transfer agent is not critical in this regard. The hydrocarbyl groups attached to the phosphorous, sulfur or nitrogen must contain a total number of carbons such that the compound is water-soluble but yet has sufficient lipophilic character to permit it to pass from the aqueous phase into a non-polar oil (or organic) phase. The compounds become disinfecting as they become lipophilic.

The hydrocarbyl groups that may be attached to the phosphorous, sulfur or nitrogen may be aliphatic aromatic, naphthenic, alkaryl or aralkyl groups. The aliphatic groups may be saturated, olefinic or acetylenic. Examples of suitable aliphatic groups are methyl, ethyl, propyl, butyl, vinyl and ethynyl. A suitable aromatic group is phenyl. Suitable alicyclic tolyl groups are cyclopropyl, cyclobutyl, cyclopentyl and cyclohexyl groups. Benzyl and phenethyl groups are suitable aralkyl groups. Suitable alkaryl groups are tolyl and xylyl groups.

The preferred positively charged phase-transfer agents are quaternary ammonium salts having hydrocarbyl groups totaling approximately 6 to ca. 30, and preferably ca. 8 to approximately 25, carbons on the quaternary nitrogen. The number of carbons on the nitrogen of the quaternary ammonium salt, as mentioned, is critical. The quaternary ammonium salt must not only be water-soluble but it must also possess sufficient lipophilic character to permit it to pass from the aqueous phase into an oil (or organic) phase. As mentioned above, when the alkaline salt containing hydrogen peroxide of crystallization is dissolved in an aqueous solution of a positively charged phase-transfer agent such as a quaternary ammonium salt, the alkaline salt extracts a proton from the hydrogen peroxide, leaving the negatively charged hydroperoxide ion. The hydroperoxide ion then becomes associated with the quaternary ammonium ion and its negative charge is effectively neutralized:

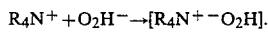

$$R_4N^+ + O_2H^- \rightarrow [R_4N^+ {}^-O_2H].$$

The resultant lipophilic quaternary ammonium hydroperoxide may then pass from the aqueous phase into an oil, or organic, phase where the hydroperoxide ion may exert its disinfecting and decontaminating effects. While quaternary ammonium salts are disinfectants and decontmminants themselves, these properties are enhanced synergistically when they are combined with a per-salt.

In the practice of this invention, a singly or doubly positively charged phase-transfer agent or a mixture of positively charged phase-transfer agents may be used. The preferred positively charged phase-transfer agents are quaternary ammonium salts wherein two of the hydrocarbyl groups attached to the nitrogen are alkyl groups of one to about three carbons, aralkyls such as a benzyl group, or any combination thereof. The remaining two hydrocarbyl groups are long chain aliphatic groups such that the total carbons on the nitrogen are not in excess of about 30, and preferably not in excess of about 25. Particularly suitable positively charged phase-transfer agents are didecyl dimethyl ammonium chloride (DDDM), tetradecyl dimethyl benzyl ammonium chloride ("DIBACTOL", manufactured by Huntington Laboratories, Inc.), tetrabutyl ammonium hydrogen sulfate, and mixtures thereof.

While the cleansing and disinfecting compositions of this invention do not require a surfactant, preferred compositions contain one or more surfactants. The surfactant disperses the material to be cleansed or disinfected, thus increasing its surface area and enhancing its contact by the quaternary ammonium hydroperoxide as well as favoring its transfer into a non-polar phase.

The surfactant used in the compositions of this invention may be a nonionic surfactant, an anionic surfactant, a cationic surfactant, or mixtures thereof. Examples of suitable nonionic surfactants are linear alkoxylates such as "TRITON X-100" (manufactured by Rohm and Haas); an alkylphenol ethoxylate such as "ICONOL OP-10" (manufactured by BASF Wyandotte Corp.); and polyoxypropylene-polyoxyethylene block copolymer, such as "PLURONIC F68LF" (manufactured by BASF Wyandotte Corp.). An example of a suitable anionic surfactant is sodium lauryl sulfate. Examples of suitable cationic surfactants are dodecyl ammonium chloride and cetyl dimethyl benzylammonium chloride.

A water-soluble, non-volatile, non-flammable glycol ether solvent such as butyl carbitol may be added in the range of five to forty percent (5%–40%) with optimum at fifteen percent (15%) to assist in dissolving and emulsifying non-polar phases, such as oils and greases.

A preferred composition of this invention contains, in addition to the per-salt, the positively charged phase-transfer agent and the surfactant, a clay or mixture of clays. It has been found that clays spread the material to be decontaminated over a large area, increasing its surface, and they also have the unique property of absorbing and also activating hydrogen peroxide and hydroperoxide ion to form free radicals such as the hydroxy radical and hydroperoxy radical which pass into the oil phase without need for a phase-transfer agent. Preferred clays in the compositions of this invention are kaolinite, attapulgite, bentonite and mixtures thereof.

It has been found that desirable rheological properties are obtained when kaolinite, attapulgite and bentonite are mixed in certain proportions. When water or an aqueous solution, such as an aqueous solution of a per-salt and a positively charged phase-transfer agent, is added to such a mixture of clay, the desired rheological properties are obtained. The mixtures of clay comprise ca. 40% to 85% by weight of kaolinite, approximately 10% to 75% by weight of attapulgite, and approximately 1% to 15% by weight of bentonite. Preferred is a mixture of approximately 50% by weight of kaolinite, ca. 40% by weight of attapulgite and approximately 10% by weight of bentonite. Such mixtures may be mixed with sufficient water or an aqueous solution to give a smooth, creamy composition having an Atterberg Number (plasticity index) within the range of approximately 15 to 75 with an Atterberg Number of ca. 30 being preferred.

The cleansing and disinfecting compositions of this invention broadly contain approximately 10% to 90% by weight of alkaline water-soluble salt containing hydrogen peroxide of crystallization, and preferably approximately 20% to 77% by weight of alkaline water-soluble salt containing hydrogen peroxide of crystallization. The compositions of the invention contain a positively charged phase-transfer agent in the broad range of from a fraction of a percent to approximately 30% by weight, and preferably in the range of approximately 1% to 23% by weight. The amount of surfactant in the compositions of the invention, if a surfactant is present, is broadly within the range of approximately 0.25% to 20% by weight, and preferably within the range of approximately 1% to 15.1% by weight.

A preferred composition of this invention contains, in addition to the alkaline water-soluble salt containing hydrogen peroxide of crystallization, the positively charged phase-transfer agent and the surfactant, a clay or mixture of clays. The amount of clay in the composition may broadly be in the range of approximatelyl 20% to 75% by weight. A preferred range is ca. 35% to 55% by weight of clay.

In addition to the foregoing, the compositions of the invention may contain other additives such as perfumes, dyes, enzymes, metal peroxides and emolients.

Thus, the instant invention provides improved cleansing and disinfecting compositions that are characterized by a number of advantages over cleansing and disinfecting compositions of the prior art. Not only are the compositions of this invention comprised of readily available and relatively inexpensive components, but the compositions are not irritating to the skin or absorbed through the skin or mucous membranes. They do not have an offensive odor and are, in fact, non-volatile. In addition, the compositions are effective against a wide variety of stains and are noncorrosive and, in many instances, anti-corrosive. They also exhibit a high level of efficacy as rapid cleansing and disinfecting agents due to the synergistic interaction of the components. Moreover, the compositions have excellent stability.

The cleansing and disinfecting compositions of this invention find utility in health care, as disinfectants in surgical applications and as cleansing and decontaminating agents. Depending on the intended use and the substrate on which they are to be used, the compositions may be formulated as creams, bulk powders, tablets, soaps, and solutions. The compositions may also be incorporated into absorbent materials such as wipes, brushes and sponges.

When the cleansing and disinfecting compositions of this invention are incorporated into an absorbent material, the choice of absorbent material may vary broadly depending on the intended use. Thus, for cleansing the skin, the cleansing and disinfecting composition may be incorporated into a cotton pad, a fabric pad or a sponge. For cleansing surfaces other than the skin, it is advantageous to incorporate the cleansing and disinfecting composition into a sponge. It is often desirable, but not essential, that the sponge have an abrasive surface.

There are presently available on the market a number of liquid detergents and solvent-based cleansers. However, these products have a number of deficiencies which are overcome by the impregnated sponges of the instant invention. For example, presently-available liquid detergents and solvent-based cleansers are not readily portable and therefore do not lend themselves to on-the-spot use or to being readily dispensed for on-the-spot use. Moreover, they are effective against only a limited variety of stains.

These deficiencies are overcome by the instant impregnated sponges. The cleansing and disinfecting compositions with which the sponges are impregnated are essentially dry. The impregnated sponges may therefore be packaged and stored almost indefinitely. They are activated for use by the addition of a solvent, most commonly water. They therefore lend themselves to being dispensed for instant use in hotel rooms, restaurants, laundry establishments, travel kits, clothing stores, fabric and sewing stores, and by airlines. Moreover, they are effective for the removal of stains such as mustard, tea, coffee, inks, dyes, blood stains, vegetable colors, juices, lipstick, dirt, grease, and oil, many of which are not removed by presently-available liquid detergents and solvents. The cleansing action of the impregnated sponges is attributable to the synergistic interaction of the components of the cleansing and disinfecting compositions along with the physical scrubbing action of the device.

The size and shape of the impregnated sponge is not critical and will vary according to its intended use. For example, the sponge may be oval, spherical, circular, square or rectangular in shape. Impregnated sponges for use on the skin will advantageously be relatively small while those intended for use on surfaces other than the skin will usually be larger.

The sponge itself may, for example, be natural sponge, expanded cellulose or a polymeric foam such as polyurethane foam. The sponge may, if desired, be colored.

While not essential, it is often desirable that at least one surface of the sponge be abrasive. This may be accomplished by cementing a porous abrasive material to at least one surface of the sponge.

The cleansing and disinfecting compositions of this invention may be incorporated into the absorbent material in a number of ways. For example, a cloth or cotton pad or a sponge may be impregnated with a solution of the cleansing and disinfecting composition and the solvent then allowed to evaporate. Alternatively, a sponge may be cut open and an interior pocket formed. The pocket is then filled with the dry cleansing and disinfecting composition and the incisions in the sponge sealed with a cement. The sponge is impregnated with a small amount of a solvent, which may have dissolved therein an additive such as a surfactant, to thereby disperse the cleansing and disinfecting composition homogeneously throughout the sponge. The solvent is then allowed to evaporate. The impregnated absorbent material is activated for use by being contacted with a solvent such as water.

The absorbent material may be impregnated with any cleansing and disinfecting composition coming within the scope of this invention. Usually, the absorbent material, e.g., sponge, will be impregnated with the maximum amount of cleansing and disinfecting composition that can be incorporated therein. Thus, the impregnated sponge may be used repeatedly, releasing an effective amount of the cleansing and disinfecting composition with each use.

In use, the impregnated absorbent material of this invention, for example, a sponge having incorporated therein the cleansing and disinfecting composition, is activated by means of a suitable solvent. The preferred solvent is water. Thus, the sponge is wet with water and used to wipe or scrub the contaminated surface. The sponge is occasionally rinsed with water as needed until the area to be treated has been cleansed or disinfected.

The efficacy of the impregnated sponges of the invention may be tested by use on a suitable stained test substrate. A one inch square of, for example, cotton, linen, nylon or silk has one quarter square inch thereof stained with one of the foregoing stains. A small impregnated sponge is treated with enough water, about 5 ml., to dissolve the cleansing and disinfecting composition and the sponge is squeezed to affect dissolution thereof. The test substrate is then scrubbed with the wet impregnated sponge.

In use, the stain or spot is scrubbed with the wet sponge and allowed to remain wet for about 15 to 30 minutes, depending on the stain. The treated area is then rinsed with water. For colored fabrics such as neckties, the entire surface should be scrubbed to prevent the appearance of a clean spot against a dirty background. The stained area is observed visually for the presence or absence of the stain or spot. The stain remover in the impregnated sponge has the advantage over bleach in that it is not corrosive, toxic, deleterious to sensitive dyes and fabrics, and is readily removed by rinsing. Moreover, it leaves no residue.

Figure 2:
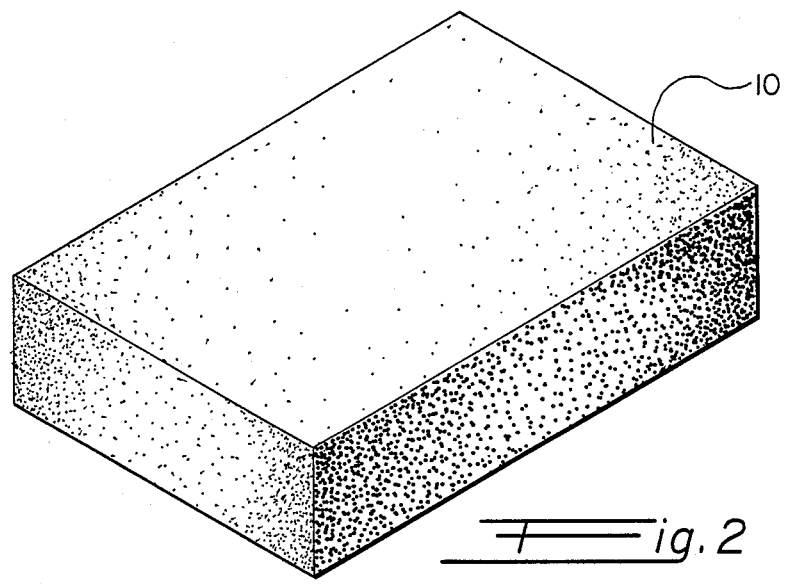
FIG. 2 is a perspective view of a sponge having incorporated therein a cleansing and disinfecting composition of the invention.

The invention will be most clearly perceived and best understood through reference to the preferred embodiments as discussed in further detail in connection with the drawings. The embodiment illustrated in FIG. 2 is a rectangularly shaped sponge 10 impregnated with the cleansing and disinfecting composition of the invention. It will be understood that the sponge may be circular, spherical, oval or square in shape. The size of the sponge will vary according to its intended use. It will also be understood that the sponge may be made of any sponge-like material For example, it may be natural sponge, expanded cellulose or polyurethane foam. If desired, the sponge may be dyed a suitable color.

Figure 3:
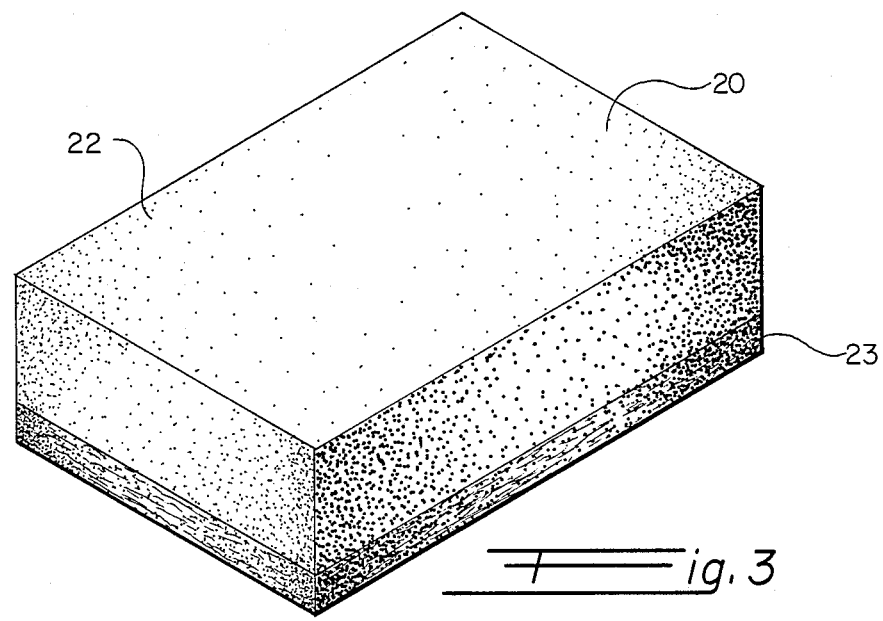
FIG. 3 is a perspective view of a sponge having incorporated therein a cleansing and disinfecting composition of the invention and wherein one surface of said sponge is a porous abrasive.

The embodiment of the invention depicted in FIG. 3 is a sponge 20 having an abrasive surface. The main body 22 of the sponge is comprised of a soft, sponge-like material having incorporated therein the cleansing and disinfecting composition of the invention. Cemented or otherwise affixed to one face of main body 22 of the sponge is a porous abrasive material 23. Sponge 20 is depicted as being rectangular in shape but, as discussed above in connection with FIG. 2, the shape and size may vary. In a preferred embodiment, main body 22 of the sponge may be comprised of a soft polymeric foam such as polyurethane foam; and the porous abrasive material 23 is a nylon hose (or suitable material) having the cleansing and disinfecting composition incorporated therein. Usually, the volume of main body 22 of the sponge 20 is much greater than that of the porous abrasive material 23. In practice, it is necessary only that the porous abrasive material 23 be thick enough not to wear out until the cleansing and disinfecting composition incorporated in sponge 20 has been exhausted.

The invention will be more clearly perceived and better understood from the following specific examples.

EXAMPLE 1

Various cleansing and disinfecting compositions were prepared by combining the following dry and liquid components in various proportions. The dry component was comprised, on a weight basis, of 30% kaolinite, 24% attapulgite, 6% bentonite and 40% sodium percarbonate. The liquid component was an aqueous solution containing 1% by weight of didecyl dimethyl ammonium chloride (DDDM), 0.1% by weight of the linear alkoxylate "TRITON X-100", and 15% by weight of butyl carbitol, a solvent that is miscible with both water and non-polar solvents.

The three clays, kaolinite, attapulgite and bentonite were combined and mixed thoroughly. The sodium percarbonate was blended into the combined clays to form a loose, homogeneous powder. When 2–4 ml. of the liquid component were added to 1 g. of the dry component, a fluid cream with desirable rheologic properties for use with a dispensing mechanism was obtained. For use on non-porous surfaces and for brush application, a ratio of 1 g. of the dry component to 1 ml. of the liquid component is satisfactory. For use on porous materials and on fabrics, as well as for use in squeeze type dispensers, a ratio of 1 g. of the dry component to 4 ml. of the liquid component is preferred.

EXAMPLE 2

A dry component comprising 75.8% by weight of sodium percarbonate, 22.7% by weight of tetradecyl dimethyl benzyl ammonium chloride ("DIBACTOL"), and 1.5% by weight of sodium lauryl sulfate was prepared. A cleansing and disinfecting solution was prepared by dissolving 1 part by weight of the foregoing dry component in 15 parts by weight of water. The resulting solution may be applied to the material to be cleansed or disinfected by brushing, spraying or immersion.

EXAMPLE 3

A dry, powdered mixture comprising 77% by weight of sodium percarbonate and 23% by weight of the quaternary ammonium salt "DIBACTOL" was prepared. The powdered mixture was introduced into an absorbent material such as a polyurethane foam, cellulose or cotton, which had been previously impregnated with a 20% by weight solution in isopropanol of the alkylphenol ethoxylate surfactant "ICONOL OP-10". The isopropanol solvent was allowed to evaporate. The resultant pad or sponge was activated by being wet with water and used to scrub or wipe, with occasional rinsing, the area to be cleansed or disinfected.

EXAMPLE 4

Sodium percarbonate was mixed with various liquid components comprising an aqueous solution of a quaternary ammonium salt and a surfactant, and the resultant decontaminating solutions were tested in the decontamination of a toxic chemical in a liquid polymer and a toxic chemical in a chlorinated hydrocarbon solvent. The decontaminating solutions were prepared by dissolving 0.4 g. of sodium percarbonate in 4 ml. of each of the liquid components. The toxic chemical compositions were 0.1 g. of benzene sulfonyl chloride in 10 g. of polymethylmethacrylate and 0.1 g. of "MALATHION" in 10 ml. of chloroform. The following table shows the weight percents of surfactants and quaternary ammonium salts in the various aqueous liquid components. The table also shows the residual activity of the toxic chemical after treatment with the various decontaminating solutions for a period of 5 minutes.

|  | Residual Toxic Activity | |
| --- | --- | --- |
| Aqueous Liquid Components | Toxic Chemical in Liquid Polymer | Toxic Chemical in Chlorinated Hydrocarbon |
| 0.1% "TRITON X-100" + 1% DDDM | negligible* | moderate** |
| 0.1% "TRITON X-100" + 1% DDDM + 15% butyl carbitol | negligible | negligible |
| 0.1% "TRITON X-100" + 1% "DIBACTOL" | negligible | moderate |
| 0.1% "TRITON X-100" + 1% "DIBACTOL" + 15% butyl carbitol | negligible | negligible. |

*negligible: 1 g.
**moderate: 5 g.

The foregoing data illustrate the efficacy of the compositions of this invention as decontaminating agents for toxic chemicals.

EXAMPLE 5

The dry component of Example 1 was mixed with the same liquid components shown in Example 4, and the resultant compositions were tested in the decontamination of a toxic chemical in a liquid polymer and a toxic chemical in a chlorinated hydrocarbon solvent. The decontaminating compositions were prepared by mixing 1 g. of the dry component with 4 ml. of each of the liquid components. The toxic chemical compositions in liquid polymer and in chlorinated hydrocarbon were the same as those described in Example 4. The following table shows the weight percents of surfactants and quaternary ammonium salts in the various aqueous liquid components. The table also shows the residual activity of the toxic chemical after treatment with the various decontaminating compositions for a period of 5 minutes.

|  | Residual Toxic Activity | |
| --- | --- | --- |
| Aqueous Liquid Components | Toxic Chemical in Liquid Polymer | Toxic Chemical in Chlorinated Hydrocarbon |
| 0.1% "TRITON X-100" + 1% DDDM | negligible* | negligible |
| 0.1% "TRITON X-100" + 1% DDDM + 15% butyl carbitol | negligible | negligible |
| 0.1% "TRITON X-100" + 1% "DIBACTOL" | negligible | negligible |

-continued

| Aqueous Liquid Components | Residual Toxic Activity | |
|---|---|---|
| | Toxic Chemical in Liquid Polymer | Toxic Chemical in Chlorinated Hydrocarbon |
| 0.1% "TRITON X-100" + 1% "DIBACTOL" + 15% butyl carbitol | negligible | negligible. |

*negligible: 1 μg.

The foregoing illustrates the efficacy of the clay-containing compositions of this invention as decontaminating agents for toxic chemicals.

EXAMPLE 6

A cleansing and disinfecting composition according to this invention was prepared by combining the following dry component and liquid component. The dry component was prepared by mixing 30% by weight of kaolinite, 24% by weight of attapulgite, 6% by weight of bentonite, 30% by weight of sodium percarbonate and 10% by weight of calcium peroxide. The liquid component was an aqueous solution containing 1% by weight of DDDM and 0.1% by weight of "TRITON X-100".

A 50% by weight solution of the pesticide "MALATHION" in xylene was diluted with xylene and placed on watch glasses so as to cover two one-inch square surfaces. Evaporation of the xylene left a 50 mg. residue of "MALATHION" on each watch glass. In triplicate runs, a slurry of 1 g. of the above dry component in 3 ml. of the above liquid component was brushed onto the watch glass and left in place for 5 minutes. Each of the three samples was then extracted with chloroform.

The cholinesterase test described by Kramer and Gamson in *Anal. Chem.*, 30, 251 (1958) was used to test for the presence of "MALATHION". A blank consisting of a xylene/chloroform solution was placed on the enzyme strip to ensure that there were no interfering substances in either solvent. The xylene solution of "MALATHION" that was placed on the watch glasses was placed on an enzyme strip and gave a positive test, i.e., the enzyme was inhibited. The three chloroform extracts from the treated watch glasses were placed on enzyme strips and, in each case, the enzyme was not inhibited. This indicates that, not only was the "MALATHION" decontaminated by the cleansing composition, but the oxidation products of "MALATHION" were not inhibitory to the enzyme.

EXAMPLE 7

Sodium percarbonate solutions of various concentrations were prepared by dissolving varying quantities of sodium percarbonate in water. Cultures of Streptococcus faecalis were treated for 10 and 20 minutes with these solutions at 25° C. and 40° C., and the percent reduction in bacteria was determined in each case. The results are shown in the following table.

| Sodium Percarbonate in Solution (ppm) | H₂O₂ in Solution (m. mol.) | Temp. °C. | % Reduction in Bacteria | |
|---|---|---|---|---|
| | | | 10 min. | 20 min. |
| 0 ppm | 0 m. mol. | 25° C. | 64.8% | 53.6% |
| 379 ppm | 3.1 m. mol. | 25° C. | 69.6% | 98.8% |
| 758 ppm | 6.2 m. mol. | 25° C. | 84.3% | 99.9999% |
| 1515 ppm | 12.5 m. mol. | 25° C. | 99.1% | 99.9999% |
| 758 ppm | 6.2 m. mol. | 40° C. | 99.9999% | 99.9999% |

The above data show that an aqueous solution of the per-salt sodium percarbonate is an effective disinfectant whose effectiveness is enhanced by increased contact time, elevated temperature and increased sodium percarbonate concentration.

EXAMPLE 8

Polyurethane surgical scrub brushes (2 in.×3 in.×1 in.) were prepared by forming interior pockets and inserting varying amounts of the powdered mixture of Example 3. After the powdered mixture was added, the incisions in the sponges were sealed with plastic adhesive. Both sides of each sponge were then impregnated with 1 ml. of a 20% by weight solution of "ICONOL OP-10" in isoproponol. The isopropanol solvent was then allowed to evaporate. The peroxide content was measured on six sequential water washings of 60 ml. each over a 10 minute period, mimicking a standard pre-operative scrub procedure. Each 60 ml. washing was collected and the peroxide content determined by permanganate titration. The results, illustrated in FIG. 1, indicate a timed release of peroxide by the dissolution of the sodium percarbonate. The treated surgical scrub sponges are seen to provide effective anti-microbial peroxide activity with repeated washing.

EXAMPLE 9

The dry component of Example 1 was mixed with aqueous solutions containing varying amounts of a quaternary ammonium salt phase-transfer agent and the resultant decontaminating compositions were used to treat various substrates contaminated with benzene sulfonyl chloride. In each case, 1.0 g. of the dry component of Example 1 was mixed with 1.0 ml. of an aqueous solution of the phase-transfer agent and the resultant decontaminating composition brought into contact with the substrate for 10 minutes. The following table gives the phase-transfer agent used, its concentration in the original aqueous solution, the substrate treated and the residual toxic contaminant on the substrate after treatment.

| Phase Transfer Agent | Concentration (ppm) | Substrate | | |
|---|---|---|---|---|
| | | Chloroform | Cloth | Greasy Cloth |
| DDDM | 10,000 | negligible | negligible | negligible |
| DDDM | 1,000 | very weak | negligible | negligible |
| DDDM | 100 | very weak | negligible | negligible |
| DDDM | 10 | strong | negligible | negligible |
| Tetrabutyl Ammonium Hydrogen Sulfate | 10,000 | negligible | negligible | very weak |
| Tetrabutyl Ammonium Hydrogen Sulfate | 1,000 | weak | negligible | very weak |
| Tetrabutyl Ammonium Hydrogen Sulfate | 100 | moderate | negligible | very weak |
| Tetrabutyl | 10 | strong | very weak | very weak |

-continued

| Phase Transfer Agent | Concentration (ppm) | Substrate | | |
|---|---|---|---|---|
| | | Chloroform | Cloth | Greasy Cloth |
| Ammonium Hydrogen Sulfate | | | | | wherein, negligible 1 μg.
very weak ca. 1-2 μg.
weak ca. 2-3 μg.
moderate ca. 3-5 μg.
strong 5 μg.

The foregoing data illustrate the effectiveness of the decontaminating compositions of this invention against toxic chemicals in various substrates.

Thus, the instant invention provides cleansing and disinfecting compositions that find utility in health care, as disinfectants in surgical applications and as cleansing and decontaminating agents. The compositions of the invention are characterized by not being irritating to the skin, by not having an offensive or irritating odor, by not being corrosive, by having excellent stability, and by being highly effective cleansing and disinfecting agents.

Depending on the end use, the compositions of the invention may be compounded in various forms. For example, they may be used as bulk powders or compressed into tablets. The compositions may also be incorporated into soaps. The components of the compositions may be mixed with a liquid such as water or an alcohol to form a cleansing and disinfecting cream or solution. In one embodiment of the invention, the cleansing and disinfecting composition is incorporated into an absorbent material such as a cotton pad, a fabric pad or a sponge. In a preferred embodiment, the impregnated sponge has an abrasive surface.

The impregnated sponges of the invention are effective against a wide variety of stains, may be stored almost indefinitely, and are activated by the addition of water. They are portable and lend themselves to being dispensed for on-the-spot use. Moreover, they are versatile, being effective stain and spot removers, degreasers, deodorizers and sanitizers on substrates such as fabrics, walls, clothing and rugs. They effectively remove stains such as inks, vegetable stains, coffee, tea, mustard and oil. Moreover, they remove mold and mildew and prevent their recurrence. In addition, they chemically neutralize odors and prevent the formation of foul smells by killing bacteria and fungus.

While specific embodiments of the present invention have been shown and described in detail to illustrate the inventive principles, it is to be understood that such showing and description have been offered only by way of example and not by way of limitation. Protection by Letters Patent of this invention in all its aspects as the same are set forth in the appended claims is sought to the broadest extent that the prior art allows.

What is claimed is:

1. A sponge impregnated with a cleansing and disinfecting composition, wherein said composition is dry and water activated and comprises an alkaline water-soluble salt having hydrogen peroxide of crystallization, a positively charged phase transfer agent wherein said water-soluble salt is selected from the group consisting of percarbonates, persilicates, perbonates and pyrophosphates, and wherein said phase-transfer agent is selected from the group consisting of quaternary ammonium salts, phosphonium salts and sufonium salts, and a surfactant.

2. The impregnated sponge of claim 1, wherein said surfactant is selected from the group consisting of anionic surfactants, cationic surfactants, nonionic surfactants, and mixtures thereof.

3. The impregnated sponge of claim 2, wherein said alkaline water-soluble salt having hydrogen peroxide of crystallization is sodium percarbonate.

4. The impregnated sponge of claim 3, wherein said positively charged phase-transfer agent is a quaternary ammonium salt having hydrocarbyl groups totaling approximately 6 to approximately 30 carbons on the quaternary nitrogen.

5. The impregnated sponge of claim 4, wherein said quaternary ammonium salt has hydrocarbyl groups totaling approximately 8 to approximately 25 carbons on the quaternary nitrogen.

6. The impregnated sponge of claim 5, wherein said cleansing and disinfecting composition comprises approximately 10% to 90% by weight of sodium percarbonate, a fraction of a percent to approximately 30% by weight of said quaternary ammonium salt, and approximately 1% to 20% by weight of surfactant.

7. The impregnated sponge of claim 6, wherein said cleansing and disinfecting composition comprises approximately 20% to 77% by weight of sodium percarbonate, approximately 1% to 23% by weight of said quaternary ammonium salt, and approximately 1.0% to 15.1% by weight of said surfactant.

8. The impregnated sponge of claim 7, wherein said surfactant is selected from the group consisting of a linear alkoxylate, an alkylphenol ethoxylate, sodium lauryl sulfate, and mixtures thereof.

9. The impregnated sponge of claim 3, wherein two of the hydrocarbyl groups on the quaternary nitrogen are selected from the group consisting of alkyl groups of one to about three carbons, aralkyl groups, and combinations thereof; and the remaining two hydrocarbyl groups are long chain aliphatic groups such that the total carbons on said nitrogen are not in excess of about thirty.

10. The impregnated sponge of claim 9, wherein the total carbons on said nitrogen are not in excess of about twenty-five.

11. The impregnated sponge of claim 8, wherein said quaternary ammonium salt is selected from the group consisting of didecyl dimethyl ammonium chloride, tetradecyl dimethyl benzyl ammonium chloride, tetrabutyl ammonium hydrogen sulfate, and mixtures thereof.

12. A surgical sponge impregnated with a cleansing and disinfecting composition, wherein said composition comprises sodium percarbonate, tetradecyl dimethyl ammonuim chloride and an alkylphenol ethoxylate.

13. The impregnated sponge of claim 1, wherein one surface thereof is comprised of kaolinite, attapulgite, bentonite and mixtures thereof, a porous abrasive and activating material.

14. The impregnated sponge of claim 1, wherein one surface thereof is comprised of kaolinite, attapulgite, bentonite and mixtures thereof, a porous abrasive and activating material.

15. The impregnated sponge of claim 1, wherein one surface thereof is comprised of kaolinite, attapulgite, bentonite and mixtures thereof, a porous abrasive and activating material.

16. The impregnated sponge of claim 1, wherein one surface thereof is comprised of kaolinite, attapulgite, bentonite and mixtures thereof, a porous abrasive and activating material.

17. The impregnated sponge of claim 2, wherein one surface thereof is comprised of kaolinite, attapulgite, bentonite and mixtures thereof, a porous abrasive and activating material.

18. The impregnated sponge of claim 3, wherein one surface thereof is comprised of kaolinite, attapulgite, bentonite and mixtures thereof, a porous abrasive and activating material.

19. The impregnated sponge of claim 4, wherein one surface thereof is comprised of kaolinite, attapulgite, bentonite and mixtures thereof, a porous abrasive and activating material.

20. The impregnated sponge of claim 5, wherein one surface thereof is comprised of kaolinite, attapulgite, bentonite and mixtures thereof, a porous abrasive and activating material.

21. The impregnated sponge of claim 6, wherein one surface thereof is comprised of kaolinite, attapulgite, bentonite and mixtures thereof, a porous abrasive and activating material.

22. The impregnated sponge of claim 7, wherein one surface thereof is comprised of kaolinite, attapulgite, bentonite and mixtures thereof, a porous abrasive and activating material.

23. The impregnated sponge of claim 8, wherein one surface thereof is comprised of kaolinite, attapulgite, bentonite and mixtures thereof, a porous abrasive and activating material.

24. The impregnated sponge of claim 9, wherein one surface thereof is comprised of kaolinite, attapulgite, bentonite and mixtures thereof, a porous abrasive and activating material.

25. The impregnated sponge of claim 10, wherein one surface thereof is comprised of kaolinite, attapulgite, bentonite and mixtures thereof, a porous abrasive and activating material.

26. The impregnated sponge of claim 11, wherein one surface thereof is comprised of kaolinite, attapulgite, bentonite and mixtures thereof, a porous abrasive and activating material.

* * * * *